United States Patent
Assad et al.

(10) Patent No.: US 10,449,672 B2
(45) Date of Patent: Oct. 22, 2019

(54) WEARABLE ELECTROMYOGRAPHY SENSOR ARRAY USING CONDUCTIVE CLOTH ELECTRODES FOR HUMAN-ROBOT INTERACTIONS

(71) Applicant: CALIFORNIA INSTITUTE OF TECHNOLOGY, Pasadena, CA (US)

(72) Inventors: Christopher Assad, Monrovia, CA (US); Jaakko T. Karras, Pasadena, CA (US); Michael T. Wolf, La Crescenta, CA (US); Adrian Stoica, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 92 days.

(21) Appl. No.: 15/445,693

(22) Filed: Feb. 28, 2017

(65) Prior Publication Data
US 2017/0259428 A1  Sep. 14, 2017

Related U.S. Application Data

(60) Provisional application No. 62/308,091, filed on Mar. 14, 2016.

(51) Int. Cl.
*B25J 9/16* (2006.01)
*A61B 5/00* (2006.01)
(Continued)

(52) U.S. Cl.
CPC ............ *B25J 9/163* (2013.01); *A61B 5/0022* (2013.01); *A61B 5/0492* (2013.01); *A61B 5/04888* (2013.01); *A61B 5/1122* (2013.01); *A61B 5/486* (2013.01); *A61B 5/6806* (2013.01); *A61B 5/6824* (2013.01); *A61B 5/7267* (2013.01); *A61B 34/74* (2016.02); *B25J 13/02* (2013.01);
(Continued)

(58) Field of Classification Search
CPC .......... B25J 9/163; B25J 13/02; B25J 13/087; A61B 5/7267; A61B 5/0022; A61B 5/1122; A61B 5/04888; A61B 5/486; A61B 5/6806; A61B 5/6824; A61B 5/0492; A61B 2560/0223; A61B 2017/00207; A61B 2562/0219; G16H 40/67; G06F 19/00; G06N 99/005; G05B 2219/36418
USPC .................................................. 700/245, 264
See application file for complete search history.

(56) References Cited

U.S. PATENT DOCUMENTS

| | | | |
|---|---|---|---|
| 2009/0171233 A1* | 7/2009 | Lanfermann | A61B 5/0488 600/546 |
| 2012/0188158 A1* | 7/2012 | Tan | A61B 5/0488 345/156 |

(Continued)

OTHER PUBLICATIONS

Assad, C. et al., "BioSleeve: a Natural EMG-Based Interface for HRI", ACM/IEEE Int. Conf. Human Robot Interaction, Tokyo, Mar. 3-6, Proc. 2013, 2 pages.
(Continued)

*Primary Examiner* — Jaime Figueroa
(74) *Attorney, Agent, or Firm* — Steinfl + Bruno LLP

(57) ABSTRACT

A sleeve worn on an arm allows detection of gestures by an array of sensors. Electromyography, inertial, and magnetic field sensors provide data that is processed to categorize gestures and translate the gestures into commands for robotic systems. Machine learning allows training of gestures to increase accuracy of detection for different users.

13 Claims, 4 Drawing Sheets

(51) Int. Cl.

| | |
|---|---|
| A61B 5/0488 | (2006.01) |
| G06F 19/00 | (2018.01) |
| A61B 5/0492 | (2006.01) |
| A61B 17/00 | (2006.01) |
| B25J 13/08 | (2006.01) |
| G06N 20/00 | (2019.01) |
| B25J 13/02 | (2006.01) |
| A61B 5/11 | (2006.01) |
| G16H 40/67 | (2018.01) |
| G05B 19/409 | (2006.01) |
| A61B 34/00 | (2016.01) |

(52) U.S. Cl.
CPC .......... B25J 13/087 (2013.01); G05B 19/409 (2013.01); G06N 20/00 (2019.01); G16H 40/67 (2018.01); *A61B 2017/00039* (2013.01); *A61B 2017/00207* (2013.01); *A61B 2034/741* (2016.02); *A61B 2560/0223* (2013.01); *A61B 2562/0219* (2013.01); *G05B 2219/35448* (2013.01); *G05B 2219/35464* (2013.01); *G05B 2219/36418* (2013.01); *G05B 2219/40195* (2013.01)

(56) References Cited

U.S. PATENT DOCUMENTS

| | | | | |
|---|---|---|---|---|
| 2013/0317648 | A1* | 11/2013 | Assad | B25J 9/1694 700/258 |
| 2014/0220422 | A1* | 8/2014 | Rogers | H01L 23/18 429/163 |
| 2015/0100135 | A1* | 4/2015 | Ives | A61B 5/6828 623/25 |
| 2015/0141784 | A1* | 5/2015 | Morun | G06F 3/015 600/372 |
| 2015/0148641 | A1* | 5/2015 | Morun | A61B 5/0492 600/372 |
| 2015/0272483 | A1* | 10/2015 | Etemad | A61B 5/0488 600/409 |
| 2015/0272501 | A1* | 10/2015 | Maceachern | A61B 5/0531 600/301 |
| 2015/0321000 | A1* | 11/2015 | Rosenbluth | A61N 1/0492 607/48 |
| 2015/0366504 | A1* | 12/2015 | Connor | A61B 5/6804 600/301 |
| 2017/0312576 | A1* | 11/2017 | Natarajan | A61B 5/1118 |

OTHER PUBLICATIONS

Dragon Runner on Qinetic North America. https://www.qinetiq-na.com/products/unmanned-systems/dragon-runner, Retrieved on Nov. 15, 2018, 7 pages.

Marine Corps Warfighting Laboratory, Futures Directorate, Quantico, VA, MCWL IROC Challenge.Ground Combat Element Branch, http://www.mcwl.marines.mil/Divisions/ScienceandTechnology/CurrentTechnologyOffice/GCE MCWLIROCChallenge.aspx, Retrieved on Nov. 15, 2018, 2 pages.

Wolf, M.T. et al., "Decoding Static and Dynamic Arm and Hand Gestures from the JPL BioSleeve," Proc.*IEEE Aerospace Conference*, Big Sky, Montana, Mar. 2-9, 2013, 9 pages.

Wolf, M.T., "Gesture-Based Robot Control with Variable Autonomy from the JPL BioSleeve", Proc. ICRA, 2013 *IEEE International Conference on Robotics and Automation (ICRA)*, Karlsruhe, Germany, May 6-10, 2013, 6 pages.

* cited by examiner

WEARABLE ELECTROMYOGRAPHY SENSOR ARRAY USING CONDUCTIVE CLOTH ELECTRODES FOR HUMAN-ROBOT INTERACTIONS

CROSS REFERENCE TO RELATED APPLICATIONS

The present application claims priority to U.S. Provisional Patent Application No. 62/308,091, filed on Mar. 14, 2016, the disclosure of which is incorporated herein by reference in its entirety.

STATEMENT OF INTEREST

The invention described herein was made in the performance of work under a NASA contract NNN12AA01C, and is subject to the provisions of Public Law 96-517 (35 USC 202) in which the Contractor has elected to retain title.

TECHNICAL FIELD

The present disclosure relates to robot control systems. More particularly, it relates to a wearable electromyography sensor array using conductive cloth electrodes for human-robot interactions.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
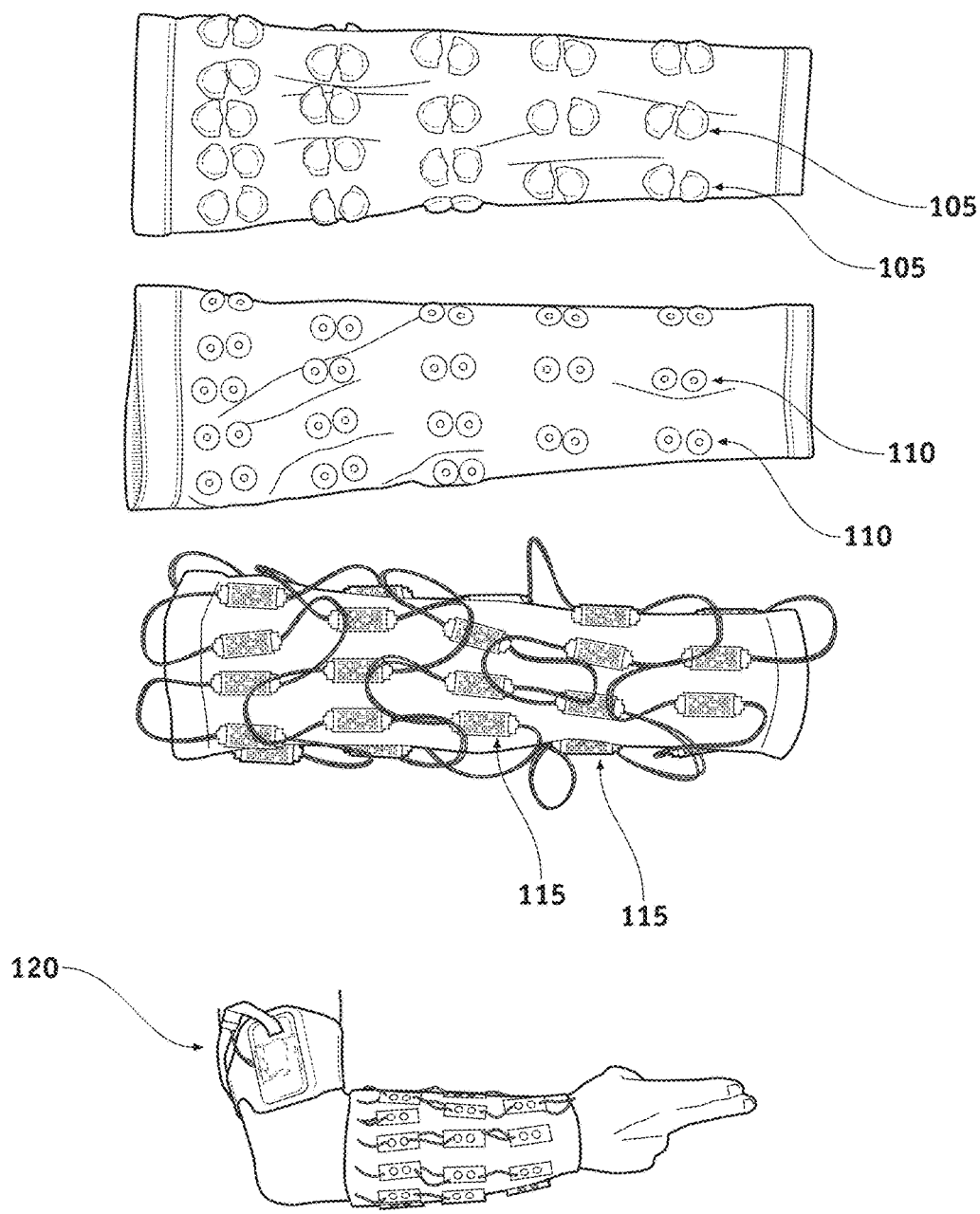
FIG. 1 illustrates a wireless BioSleeve prototype.

In a first aspect of the disclosure, a device is described, the device comprising: a plurality of electrodes attached on an inner surface of an elastic sleeve and configured to detect electric signals on a skin; a plurality of electromyography sensors on an outer surface of the elastic sleeve, the plurality of electrodes being electrically connected to the plurality of electromyography sensors through the elastic sleeve; and at least one inertial measurement unit attached to the elastic sleeve and configured to detect an orientation of the elastic sleeve.

In a second aspect of the disclosure, a method is described, the method comprising: providing a device to be worn on a forearm, the device comprising: a plurality of electrodes attached on an inner surface of an elastic sleeve, a plurality of electromyography sensors on an outer surface of the elastic sleeve, the plurality of electrodes being electrically connected to the plurality of electromyography sensors through the elastic sleeve, at least one inertial measurement unit attached to the elastic sleeve, and a processor; detecting electric signals on a forearm skin by the plurality of electromyography sensors; detecting an orientation of the forearm by the at least one inertial measurement unit; categorizing muscle activations in the forearm into corresponding hand and forearm gestures, based on the detected electric signals and orientation; and issuing commands to a robotic system based on the hand and forearm gestures

DETAILED DESCRIPTION

The present disclosure describes a wearable electromyography sensor array using conductive cloth electrodes for human-robot interaction (HRI) interfaces. The wearable sensor array can also be termed as a BioSleeve for gesture-based control.

The BioSleeve is a wearable gesture-based human interface for natural robot control. The activity of the user's hand and arm that is wearing the sleeve can be monitored via surface electromyography sensors and inertial measurement units (IMU, comprised of gyrometers, accelerometers, and magnetic field sensors). The array of electromyography and IMUs can be embedded in a forearm sleeve, with the sensors being distributed on an array of locations along the sleeve. Gesture recognition software can then decode the sensor signals, classify gesture type, and map the result to output commands to be sent to a robot. In some embodiments, the BioSleeve system can accurately and reliably decode twenty or more discrete hand and finger gestures and estimate the continuous orientation of the forearm. The BioSleeve can also be implemented as a wireless system that enables portable field use. In the following example, gesture-based commands were developed to control an exemplary tracked robot, including driving the tracks, a 4 degree-of-freedom manipulator and a pan/tilt mast for a stereo camera. In other embodiments, the BioSleeve may be configured to control different robots.

Gestures can be sent in several modes, as detailed in the following examples. For example, supervisory point-to-goal driving commands, virtual joystick for teleoperation of driving and arm, mimicked manipulation of the arm, and pan-tilt of the camera. Hand gestures and arm positions can be mapped to various commands recognized by the robot's onboard control software, and are meant to integrate with the robot's perception of its environment and its ability to complete tasks with various levels of autonomy. The portable BioSleeve interface was demonstrated through control of a robot during participation in field trials, such as the Intuitive Robotic Operator Control Challenge. The successful completion of all Challenge events demonstrated the versatility of the system to provide multiple commands in different modes of control to a robot operating under difficult real-world environmental conditions. Robots are becoming more capable and ubiquitous in environments shared with humans, increasing the need for natural, intuitive, and flexible human-robot interaction (HRI) systems. The present disclosure describes a wearable, robust, robot control interface that captures natural arm, hand and finger gestures for applications in telesupervision and teleoperation. The BioSleeve interface is designed to incorporate an array of surface electromyography (EMG) sensors and inertial measurement units (IMUs) into an easily donned, low profile package worn on the user's forearm. By monitoring the forearm muscles, the BioSleeve can achieve detailed tracking of the fingers and hand without requiring hand-worn equipment, while the IMUs provide information on arm motion and position.

Potential applications include astronauts commanding of construction robots on the moon, operators of urban search and rescue robots, soldiers directing bomb disposal or scout robots, and amputees controlling highly dexterous hand prostheses. For these mobile field applications, the combination of EMG and IMU sensors worn on the body has advantages over other methods of gesture recognition, such as computer vision with external cameras (which works best in controlled environments), or using glove-based systems with inertial and/or position sensors (which obtrusively cover the hand). Unlike other gesture recognition systems, use of the BioSleeve for robot control is invariant to most types of noises that affect human-machine interfaces: lighting conditions, occlusions, and acoustic noise (for voice interfaces), and does not constrain the human-robot spatial relationship, nor does it encumber the user's hands. Besides leaving the hands free, the BioSleeve EMG sensors provide data regarding not only to the hand/finger positions but also the muscle forces, information that can be used in the robot control paradigm of the present disclosure, but that is unavailable to inertial or visual sensors alone.

Previous BioSleeve prototypes were tethered to a desktop computer, see Refs. [1-3]. The present disclosure reports development of a new wireless BioSleeve prototype that is meant for portable field use, with no external sensors observing the human from proximity (e.g., cameras, microphones). In addition, a robot control software layer with several command modes was incorporated in the BioSleeve system described herein, including modes such as teleoperation of mobility, manipulator arm and camera pan/tilt movements, and telesupervision (e.g., point-to-goal) for robot navigation. The improved BioSleeve interface was tested on an exemplary robot, which was programmed with modular software to receive and respond to BioSleeve commands. The BioSleeve operation was validated through testing in several outdoor and indoor noisy environments simulating urban disaster scenarios. The results reported herein demonstrate that this system can improve Hill with applicability to a wide range of real-world environments.

FIG. 1 illustrates a wireless BioSleeve prototype, comprising dry conductive cloth electrodes on its inner side (105), snap buttons on the outside for contact to sensor circuits (110), and custom bipolar EMG sensors (115) mounted on the electrode snaps. The inner conductive cloth can conduct electrical signals from the skin to the sensors mounted outside on the snap buttons. In other embodiments, different implementations may be used for the sensors to detect the electrical signals on the skin while being attached on the sleeve in a useful and comfortable manner. Sensor data collected from the sleeve worn on the forearm (125) can be processed with embedded computational electronics worn either in the sleeve on other parts of the body, such as the upper arm (120).

The BioSleeve concept is designed to enable detailed, high degree-of-freedom (DOF) arm and hand tracking by integrating: (1) an array of dry-contact active surface EMG sensors to monitor muscle activations in the forearm, (2) IMU/magnetic field sensor(s) to estimate limb orientation with respect to the body, and (3) in-sleeve processing for data collection, gesture recognition, command generation, and wireless communication to the target robot. The previous tethered prototypes were demonstrated in control of 5 different robotic platforms, but only in a lab environment. To make the system portable, in-sleeve processing was added, for feature extraction and wireless communication to an external laptop. A more general robot command interface was also built, to allow various command modes.

An exemplary BioSleeve is shown in FIG. 1. In some embodiments, it can incorporate 32 (or more) bipolar surface EMG sensors, which employ dry-contact conductive cloth electrodes. This specific embodiment can be considered an intermediary implementation, while other embodiments can completely embed the sleeve into a clothing garment, with no exposed electronic components to the surface. For example the external clothing garment could provide protection for the electronics, such as mechanical protection in case of bumps, or weather protection such as waterproofing. The sensor array can be positioned, in some embodiments, on the proximal forearm near the elbow, to monitor activation of the forearm muscles. These EMG signals contain a combination of force and position information for the wrist, hand and fingers. Dry-contact electrodes have advantages over conventional wet (silver chloride gel) adhesive electrodes in ease of use, as they can slide across the skin, and be embedded in garments which can be quickly donned. In this embodiment, the sensors were packaged in a tight-fitting elastic sleeve to provide constant mechanical pressure on the users arm and maintain good skin contact.

To complement the EMG sensor array, in some embodiments a small IMU sensor can also be mounted on the BioSleeve to monitor forearm motion with respect to the body. Optionally, additional IMUs can be strapped to the upper arm and torso for full arm monitoring. The IMUs can comprise and fuse data from a 3-axis gyroscope, 3-axis accelerometer, and 3-axis magnetometer. Such data enables model-constrained pose estimation of the limb segments. Combined with the EMG array, IMU sensors can provide sufficient information to distinguish gestures from a large set of high DOF arm and hand motions.

The new BioSleeve prototype also has a custom designed pre-processing board that can be mounted on the upper arm with a battery for power (120). The board, in some embodiments, can sample data from up to 32 EMG channels at 2000 samples per second per channel, compute the standard deviation of each channel over a rolling window in time, and use a wireless communication protocol, such as Bluetooth™, to transmit these features at 100 ms intervals to a nearby laptop or other type of mobile computer, for further processing. For example, mobile computers may comprise smartphones and tablets. The board can also collect data from several of the IMU sensors and transmit it with the EMG data.

The BioSleeve gesture recognition software has been described in previous publications, see Refs. [2,3]. The software can receive either raw data or features extracted from the sensor array hardware, and can perform pattern recognition based on a Support Vector Machine classifier. In some embodiments, the user first chooses a gesture library (e.g., the library illustrated in FIG. 2), and then is guided through a training session that consists of holding a static pose for 6-10 seconds for each gesture. In some embodiments, the system has been used to reliably decode as many as 20 discrete hand and finger gestures with ≥95% accuracy up to an hour after training, and to estimate the continuous orientation of the forearm in heading, pitch and roll. This software currently runs on an external laptop or it can be embedded with a processor in the sleeve. Therefore, in some embodiments the sleeve may comprise the processing computer without requiring an external mobile computer.

With the pre-processing board transmitting EMG features to an external laptop computer for gesture recognition, the system performance appears qualitatively similar to that of our previous wired versions having the same number and placement of sensors. However, the wireless version can exhibit fewer movement artifacts (likely due to no tether drag), and less susceptibility to 60 Hz power-line artifacts.

Figure 2:
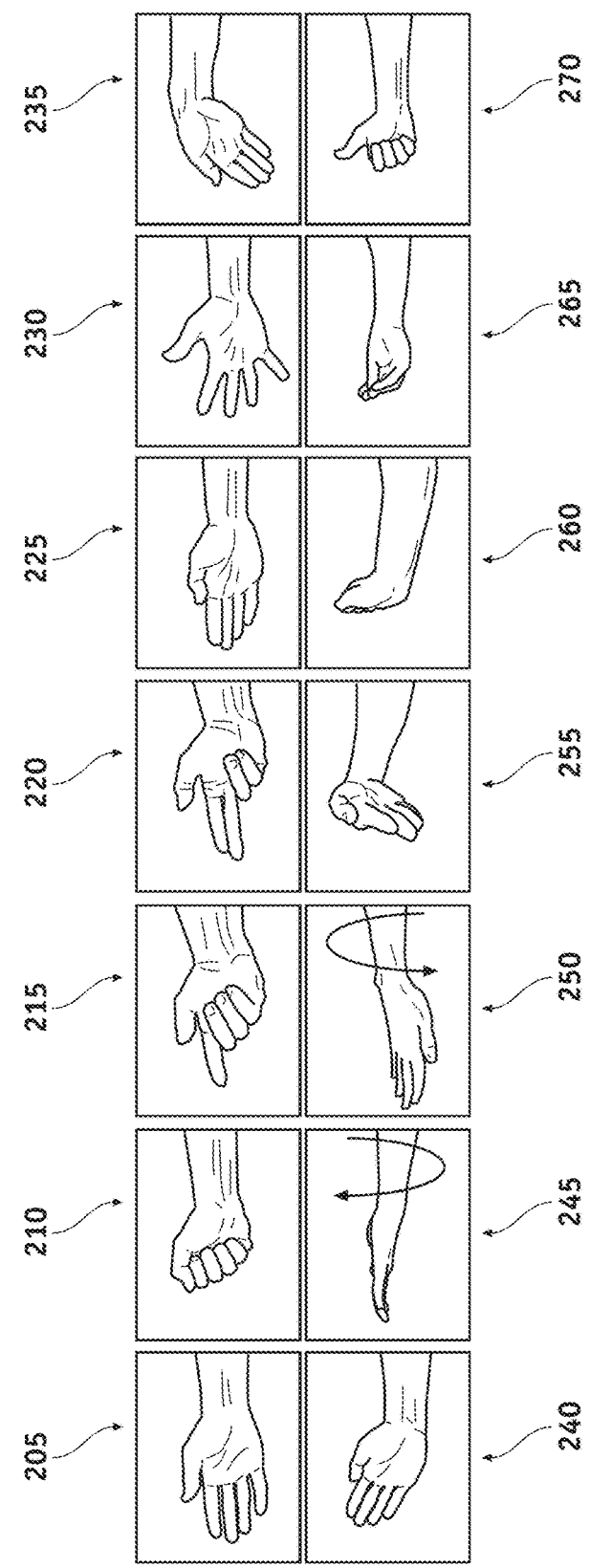
FIG. 2 illustrates an exemplary gesture library.

FIG. 2 illustrates an exemplary gesture library used in the IROC Challenge field trials: Rest (205), Fist (210), Point 2 (215), Point 2-3 (220), Adducted 1-5 (225), Abducted 1-5 (230), Ulnar Deviation (235), Radial Deviation (240), Wrist Supination (245), Wrist Pronation (250), Wrist Flexion (255), Wrist Extension (260), Pinch All (265), Thumb Back (270).

The array of channels, or sensors, on the sleeve may give a unique EMG signal pattern for a specific gesture. However, there may be a degree of variation, for the same gesture, in the EMG signals detected. Therefore, training allows the software to group different readings with small degrees of variation into one group, corresponding to one gesture. These readings in one group are classified as one gesture. After training, the gesture can be detected according to the classification. Therefore, it can be helpful for the user to train the sleeve before actual usage. For example, machine learning algorithms can be used to classify gestures.

In some embodiments, the graphical interface (GUI) of the software for gesture recognition may comprise raw data traces, channel features bar chart and heat map, clustered training data, and control buttons for training and robot connections.

After the classifier software is trained on a gesture library, the user can connect to a remote robot or robots to send commands in several modes. This can be performed through a separate robot control GUI on the same laptop that performs the gesture recognition, for the embodiments that utilize a laptop. Each robot has its own configuration file that defines its allowable commands, control modes, and the mapping from gestures to commands. In some embodiments, a standard may be developed so that any robot which adheres to the standard may be connected to the BioSleeve by accepting a standard configuration file.

In some embodiments, the robot control GUI communicates commands via WiFi TCP-IP to software control modules that reside on the robot's computer. Table 1 shows an exemplary mapping between gestures, the intended robot behaviors, and the actual command module implementation of the behaviors.

TABLE 1

| Behavior | Gestures | Robot Command Tracked mobility | Mode |
| --- | --- | --- | --- |
| Teleop tracks - continuous | Hold gesture for desired duration. Forward: Point-2 or Point-23 Backward: Ulnar deviation Turns: Wrist flexion and extension | TRACKS left_vel right_vel duration | TRACK-TELE |
| Teleop tracks - step (time) | Make brief gesture as above | TRACKS left_vel right_vel duration | TRACK-TELE |
| Halt | Fist (or Palm) up at face level, facing forward | HALT | all |
| Set current heading | Point to heading with thumb up | SET_HEADING yaw_angle | TRACK-SUP |
| Go that way | Point to heading then pronate 90 deg with all fingers adducted | NAV_HEADING yaw_angle speed | TRACK-SUP |
| Set rally point | Point to spot on ground, then make fist | SET_RALLY | TRACK-SUP |
| Navigate to rally point | Put arm in air with elbow at 90 deg, make circular motion with Point-2 or Point-23 | NAV_RALLY | TRACK-SUP |
| Navigate to pointed object/ground location | Point to heading then pronate 90 deg with all fingers adducted | NAV_RAY_INTERSECT pitch yaw shoulder_pos speed | TRACK-SUP |
| Head/Neck controls | Tilt up/down: Radial and ulnar deviation Pan right/left: Wrist flexion, wrist extension | HEAD direction degrees | HEAD |
| End Effector Teleop | Forward: Point-2 or Point-23 Backward: Thumb up pointed back Up/Down: Radial and ulnar deviation Right/left: Wrist flexion, wrist extension | EE_POS x_vel y_vel z_vel duration | ARM |
| Rotate wrist | Wrist Pronation/Supination | EE_ROTATE theta_vel duration | ARM |
| Grasp control | Open: Hand abduction, Close: Pinch All | EE_ GRASP 0/1 (open/close) | ARM |
| Home the arm | (button only) | ARM_HOME | ARM |

In other embodiments, mappings different from that of Table 1 may be used. In Table 1, the robot behavior is described in the $1^{st}$ column, while the corresponding gesture is described in the $2^{nd}$ column. For example, by pointing a spot on the ground and closing the hand in a fist, the sleeve can translate the gesture into a command for the robot, setting a rallying point.

In some embodiments, the robot may comprise tracks for movements over a variety of terrains, as well as a multiple degree of freedom manipulator, such as a 4 DOF manipulator, a gripper to hold onto objects, and a stereo camera. In other embodiments, different types of equipment and sensors may be mounted on the robot and activated with corresponding gestures.

For example, a small (20 lb) unmanned tracked ground vehicle may be used as described in Ref [4]. This exemplary robot carried a 4-DOF manipulator arm with gripper, a stereo camera on a small mast mounted to the base of the arm, two onboard computers, and an IMU in the base. Robot control modules resided on the robot's internal computer. An additional mini computer was mounted underneath the arm to run stereo processing and visual odometry software for the stereo data. The robot also carried two lithium ion batteries on board, one for the control and drive of the tracks and arm, the second for the mini computer and cameras.

The embodiment of the BioSleeve commanding the exemplary robot described above was tested in the Intuitive Robotic Operator Control (IROC) Challenge (see Ref [5]), organized by the Marine Corps Warfighting Lab (MCWL) at the Muscatatuck Urban Training Center (MUTC) in Indiana. The event's goal was to demonstrate technologies that could provide soldiers with the ability to control an unmanned ground vehicle. MUTC has many different disaster zones (e.g., simulating flood zone, embassy, prison, earthquake, etc.) for training first responders, military urban warfare and special operations forces. There were three challenges: Command Challenge—The goal was to demonstrate recognition of commands in a static indoor setting. Mission Execution Challenge—The goal was to guide a mobile robot through two 200 m outdoor courses over dirt roads with obstacles, in a "shanty town" setting. The main performance metric for this challenge was to minimize the number of interactions between the operator and robot. Companion Challenge—The goal was to guide a mobile robot through several rooms of an indoor challenge in a mock "prison compound", to test robustness of the command interface to conditions of poor visibility and/or audible (e.g., smoke, dark, battle noise, crowd noise). The main performance metric for this challenge was to minimize time to completion.

To evaluate the BioSleeve system performance in a real-world condition, the BioSleeve team entered the IROC Challenge. For the Command Challenge, the sleeve was used to recognize the 14 gestures listed in FIG. 2, each performed 5 times as directed by the event judges. The system scored 100% accuracy, correctly reporting all 70 gestures.

For the Mission Execution Challenge, the robot was run mainly in telesupervision mode. For example, during the event the Set Heading, Navigate To and Adjust Left and Adjust Right commands were used. These commands allowed the robot to drive long distances with few manual adjustments to adjust the heading, most often on turns or to navigate around obstacles. This helped satisfy the performance metric for this event, which was to minimize the number of interactions between the human and robot. Adding more onboard autonomy (such as hazard avoidance) would have helped for this challenge by alleviating the need for using controls for small trajectory adjustments around obstacles.

For the Companion Challenge, the robot was run mainly in teleoperation mode, using commands Forward, Turn Right, and Turn Left. Some of the rooms that had to be navigated were: a smoke filled room, a room with crowd/wind noise, a room with battleground noise, and a room in darkness. All rooms also had obstacles to be negotiated. The rooms with audible noise had no effect on the system performance, and were completed with fast traverses. The smoke and dark rooms presented a small challenge due to the limited vision of the human operator, but none for the communications or robot performance. Each room took several minutes to navigate, as the robot was operated only at low-medium speeds, and there were a handful of false positive recognitions resulting from movement artifacts or inadvertent operator actions. The course was completed well within the maximum allocated time of 2 hours, and must have been one of the fastest since there was no interference in commands, and only limited influence on visual feedback; by comparison, a voice-command system tested as part of a different technology demonstration was seriously affected by noise.

The present disclosure describes an improved BioSleeve system that enables humans to send commands to a robot using natural gestures. By capturing EMG and IMU signals from a forearm-worn BioSleeve, it is possible to extract accurate information about the hand position and gross arm position, without the limitations of vision systems and without requiring hand-worn equipment. The field trial results reported here using the portable BioSleeve prototype demonstrated the versatility of the system to provide many types of commands in different modes of control to a robot operating under various real-world environmental conditions. The gesture recognition and command mapping software can also be implemented with all in-sleeve processing, allowing the BioSleeve to communicate gesture-based commands directly to the robot with no intermediates.

The system described herein can have the following properties:

Ease-of-use: The BioSleeve can be conveniently embedded into wearable garments, donned and doffed as part of daily clothes, and worn unobtrusively by the operator. No extra setup time is required for placement of individual electrodes, fine alignment, etc.

Free mobility: In some embodiments, there are no external sensors, hand obstructions, or electrode wires imposing constraints on allowable movements.

Reliability: Large dense sensor arrays can add redundancy and are more immune from movement artifacts (electrode slippage, etc.), with the potential to dramatically improve decoding reliability.

Durability: Active channel selection and low power consumption per channel enables operation for long periods of time on in-sleeve batteries.

Versatility: The output of the gesture recognition can be mapped into various command libraries for different robotic platforms, or for different control modes within a single system, such as those detailed above.

In some embodiments, conductive cloth (such as nylon/silver) fabric electrodes can be stitched or snapped directly into an elastic sleeve to fabricate the BioSleeve. In such a way, it is possible to increase contact robustness, comfort, durability, and electrode density. In some embodiments, 32 bipolar channels (64 total electrodes) can be used. However, a different number of channels or electrodes may also be used.

Figure 4:
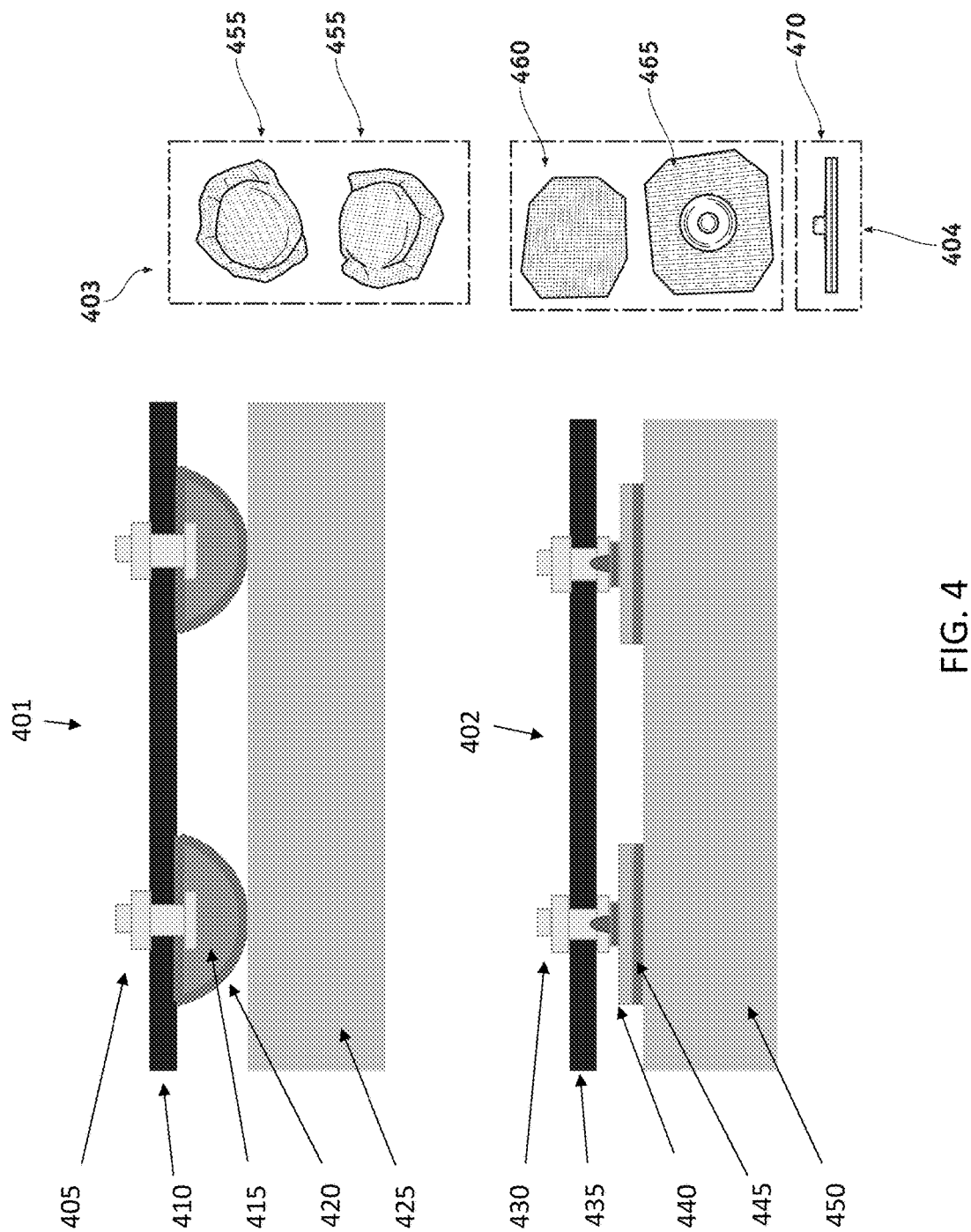
FIG. 4 illustrates exemplary electrodes.

FIG. 4 illustrates two exemplary cloth electrode cross sections. For one embodiment (401), the forearm is illustrated (425), where the electrodes can read EMG signals on the skin. The conductive cloth (420) is wrapped around a rubber or foam insert (415), which allows pressing of the electrodes on the skin without discomfort. An elastic layer (410) allows pressing of the sleeve on the forearm. The snap fasteners (405) allow electrical and mechanical connection to the electronics located on the sleeve, from one surface of the sleeve through to the opposite surface. In one embodiment (403), the conductive cloth electrode (455) is further sewn to the sleeve fabric for robustness. In another embodiment (402), the electrodes again make contact with the forearm skin (450), but the conductive cloth (445) is now applied directly to the surface of a standard commercial adhesive gel silver/silver chloride electrode (440). The electrode is snapped onto a snap fastener (430) that allows electrical and mechanical connection to the electronics located on the sleeve. The elastic layer (435) again allows pressing of the electrodes on the forearm to maintain contact with the skin. Another embodiment (404) illustrates the contact-side (460), snap side (465), and a side view (470) of this electrode type.

As known to the person of ordinary skill in the art, commercial EMG electrodes typically use Ag/AgCl adhesive gel to make good contact with the skin, but such electrodes are sticky, and therefore difficult to don in large arrays. Another drawback is that such electrodes tend to dry out after several hours. The BioSleeve's large array of EMG electrodes has a requirement to retain good contact with the skin, while maximizing ease-of-use: comfortable for long wearing duration, maintains signal quality for longer duration, and easy to slide on/slide off for donning the sleeve.

The present disclosure describes how to incorporate conductive cloth fabric at the surface of the electrode to make dry-contact electrodes that can slide easily over skin and are comfortable to wear, but retain sufficient signal quality. The conductive cloth electrode array can be embedded in an athletic compression sleeve to help maintain sufficient ohmic contact with the skin.

Embodiments of the two different cloth electrodes above are described in the following, and compared to conventional EMG electrode types. In one embodiment (Type I), the electrodes use conductive cloth (with commercial fabric made from nylon and silver thread) attached directly to the front of a conventional Ag/AgCl adhesive gel electrode that has a snap button connector on the backside. This embodiment allows use of the same connectors/infrastructure used in conventional EMG recording systems, while enabling the electrodes to slide over the skin. This embodiment also slows the rate at which the conductive gel dries so that the useful electrode lifetime is increased.

In another embodiment (Type II), the electrodes use conductive fabric wrapped around a non-conductive foam pad, and riveted through the sleeve material with button snaps as can be found in standard clothing. In both embodiments the button snaps conduct the EMG signal to the EMG amplifier circuit on the outside of the sleeve. Both embodiment designs were tested against conventional Ag/AgCl electrodes, and were found to achieve qualitatively similar EMG signal quality and signal/noise ratios. Schematic diagrams and pictures of the prototypes are shown in FIG. 4.

Figure 3:
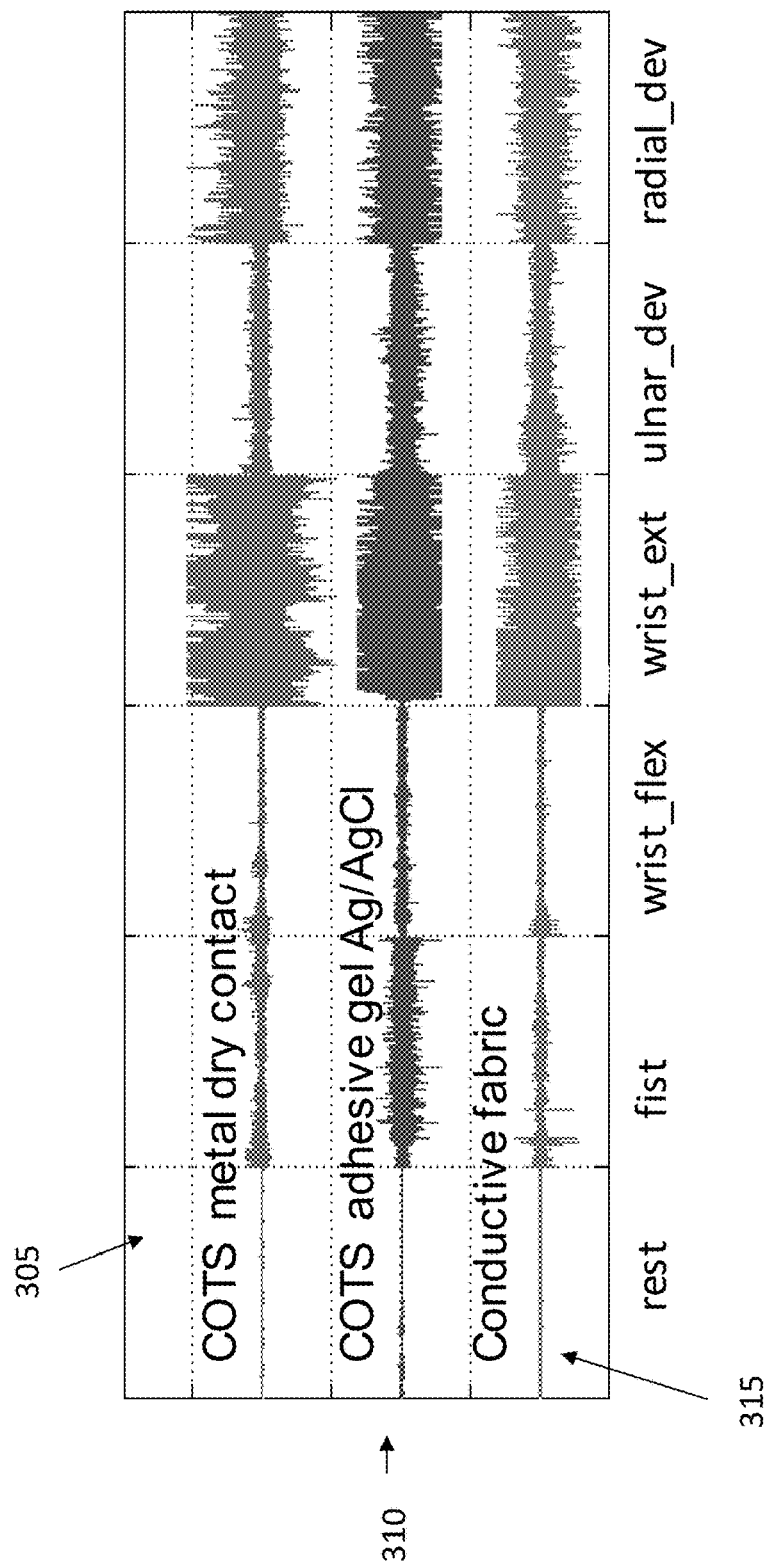
FIG. 3 illustrates a comparison between electrodes.

The conductive cloth electrodes and custom-built EMG sensors were evaluated against both commercial EMG sensors and standard wet adhesive Ag/AgCl EMG electrodes. In FIG. 3, the resulting data is illustrated for dry contact electrodes (305), adhesive gel (310), and conductive fabric (315). There appears to be no significant difference between types of electrodes in S/N ratios or qualitative differences in analog signal quality, as long as adequate contact pressure was maintained to keep good contact with the skin.

The EMG electrodes described herein have several advantages over conventional electrodes. Conventional electrode types fall into three general categories: adhesive electrodes with a conductive gel interface, dry-contact metal electrodes, and conductive cloth electrodes. The conductive gel adhesive electrodes are the most common in commercial and clinical use, but must be individually mounted and tend to dry out over the course of a few hours, thereby degrading the EMG signal. Dry-contact metal electrodes must be pressed against the skin to maintain good ohmic contact, which makes them uncomfortable to wear over long periods of time. Dry-contact metal electrodes are also susceptible to signal degradation from the effects of sweat at the interface. Conventional conductive cloth electrodes are used mainly in research on prosthetic interfaces and are not yet readily available. These electrodes require compression like those described herein, but have issues with sweat wicking up the leads to the amplifier electronics and shorting the signal between electrode pads.

The conductive cloth electrodes described in the present disclosure combine several advantages of the conventional electrodes above while avoiding most of their disadvantages. The conductive cloth electrodes described herein have a dry-contact interface with the skin, and are therefore easier to don in a large array compared to the conventional adhesive gel electrodes. The conductive cloth electrodes described herein also have longer useful lifespan. These electrodes are more comfortable to wear than the dry-contact metal electrodes. The conductive cloth electrodes described herein are also more robust, compared to conventional metal or cloth electrodes, against the effects of sweat on the electrode-skin interface.

The conductive cloth electrodes described herein use a snap button riveted through the sleeve, therefore sweat cannot wick through to short or corrode the amplifier electronics. The conductive cloth electrodes described herein are also embedded in a commercial athletic sleeve that is designed to wick sweat away from the skin, so the sleeve should lessen the effects from sweat shorting across electrodes.

The conductive cloth electrodes described herein can be used for gesture control interfaces to control robotics systems, which are useful in many human-robot interactions and telerobotic systems. For example, robotic arms and assistants in space applications can benefit from using a BioSleeve or similar system.

The BioSleeve can also comprise a software interface to analyze and interpret gestures. The software collects data from an array of sensors (EMG and IMU) worn on a person's arm, while the person is performing hand and arm gestures. The software can then performs calibration and training to learn a set of gestures from the sensor data. After training, the software performs real-time gesture recognition to classify arm and hand gestures. After classification, the gestures can be mapped to robot control commands and sent to a particular robot specified by the user.

The overall system can therefore comprise reading in large array of data from sensors spread over arm, then learning and classifying gestures in real-time with advanced pattern recognition/machine learning techniques, and subsequently mapping the results to a robot command library.

Current Human-Machine Interfaces, particularly those designed to control high degree-of-freedom robots, are bulky, usually obstructing the users hands, and non-intuitive, requiring a lot of training. The software of the BioSleeve is meant to make reading natural hand gestures more reliable and practical for uses in human-machine interfaces and prosthetic interfaces.

The software can first control an analog-digital converter to digitize and read the raw EMG and IMU sensor data from the BioSleeve. After donning the BioSleeve, the user can be instructed to hold each of N gestures for a brief period. For example, N can be between 10 and 20, and the training period can be about 6 seconds. A feature vector is extracted from a sliding window of prior data on each channel, related to the signal power in the EMG data (or orientation of the IMUs). The code can use the standard deviation to provide a good measure of muscle activity, as it is correlated to the signal amplitude but invariant to offsets. The labeled features collected in this calibration session are used to train a machine learning algorithm for pattern recognition. For example, the code can support two methods, a multi-class support vector machine classifier (SVM), and a Random Forests classifier (RF). However, additional methods may be implemented. After training, new gestures can be classified in real-time, and mapped to a user-defined set of robot control commands. Some command types utilize the BioSleeve output for direct teleoperation, while others send supervisory commands using simple gestures. In some applications, the BioSleeve can be used to control interfaces for prosthetic arms.

In some embodiments, the sleeve may be used to control non-robotic physical systems, such as for example motorized wheelchairs, surgical arms and other systems. The IMU sensor is configured to detect an orientation of the arm. Since the sleeve is attached to the arm during operation, the IMU is equally configured to detect the orientation of the sleeve while being worn on the arm. In some embodiments, the robotic system is a virtual system which can be controlled in a similar manner as a physical robot. For example, an avatar or other simulated system may be controlled with the sleeve. For example, in virtual reality settings.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] M. T., Wolf, C. Assad, M. T. Vernacchia, J. Fromm, H. L. Jethani, "Gesture-Based Robot Control with Variable Autonomy from the JPL BioSleeve," Proc. ICRA 2013, May 6-10, Karlsruhe, Germany,
[2] C. Assad, M. T. Wolf, A. Stoica, T. Theodoridis, K. Glette, "BioSleeve: a Natural EMG-Based Interface for HRI." Proc. 2013 ACM/IEEE Int. Conf. Human Robot Interaction, March 3-6, Tokyo.
[3] M. T. Wolf, C. Assad, A. Stoica, K. S. You, H. L. Jethani, M. T. Vernacchia, J. Fromm, Y. Iwashita, "Decoding Static and Dynamic Arm and Hand Gestures from the WI, BioSleeve," Proc. 2013 IEEE Aerospace Conference, March 2-9, Big Sky, Mont.
[4] Dragon Runner on Qinetic North America website: https://www.qinetiq-na.com/products/unmanned-systems/dragon-runner
[5] MCWL IROC Challenge website: http://www.mcwl.marines.mil/Divisions/ScienceandTechnology/Current TechnologyOffice/GCE/MCWLIROCChallenge.aspx

What is claimed is:

1. A device comprising:
a plurality of electrodes attached on an inner surface of an elastic sleeve and configured to detect electric signals on a skin;
a plurality of electromyography sensors on an outer surface of the elastic sleeve, the plurality of electrodes being electrically connected to the plurality of electromyography sensors through the elastic sleeve; and
at least one inertial measurement unit attached to the elastic sleeve and configured to detect an orientation of the elastic sleeve,
wherein each electrode of the plurality of electrodes comprises conductive cloth wrapped around a foam or rubber insert, and a snap-on attachment configured to mechanically and electrically connect to a corresponding electromyography sensor through a corresponding opening in the elastic sleeve.

2. The device of claim 1, further comprising a processor configured to process data from the plurality of electromyography sensors and from the at least one inertial measurement unit to detect hand and forearm gestures.

3. The device of claim 2, wherein the processor comprises a gesture recognition software to decode the sensor signals, classify gesture type, and map the result to output commands to be sent to a robot.

4. The device of claim 1, wherein the at least one inertial measurement unit comprises a 3-axis gyroscope, 3-axis accelerometer, and 3-axis magnetometer.

5. The device of claim 1, wherein the at least one inertial measurement unit comprises a plurality of inertial measurement units.

6. The device of claim 1, wherein the conductive cloth comprises nylon and silver.

7. A device comprising:
a plurality of electrodes attached on an inner surface of an elastic sleeve and configured to detect electric signals on a skin;
a plurality of electromyography sensors on an outer surface of the elastic sleeve, the plurality of electrodes being electrically connected to the plurality of electromyography sensors through the elastic sleeve; and
at least one inertial measurement unit attached to the elastic sleeve and configured to detect an orientation of the elastic sleeve,
wherein each electrode of the plurality of electrodes comprises conductive cloth attached to one side of an electric gel pad, and a snap-on attachment on an opposite side of the electric gel pad, to mechanically and electrically connect to a corresponding electromyography sensor through a corresponding opening in the elastic sleeve.

8. A method comprising:
providing a device to be worn on a forearm, the device comprising:
a plurality of electrodes attached on an inner surface of an elastic sleeve, a plurality of electromyography sensors on an outer surface of the elastic sleeve, the plurality of electrodes being electrically connected to the plurality of electromyography sensors through the elastic sleeve, at least one inertial measurement unit attached to the elastic sleeve, and a processor;

detecting electric signals on a forearm skin by the plurality of electromyography sensors;

detecting an orientation of the forearm by the at least one inertial measurement unit;

categorizing muscle activations in the forearm into corresponding hand and forearm gestures, based on the detected electric signals and orientation; and issuing commands to a robotic system based on the hand and forearm gestures, wherein each electrode of the plurality of electrodes comprises conductive cloth wrapped around a foam or rubber insert, and a snap-on attachment to mechanically and electrically connect to a corresponding electromyography sensor through a corresponding opening in the elastic sleeve.

9. The method of claim 8, further comprising providing a library of hand and forearm gestures corresponding to commands for the robotic system.

10. The method of claim 9, further comprising training the device to categorize the hand and forearm gestures by instructing a user to perform each hand and forearm gesture in the library for a set number of times and a set period.

11. The method of claim 8, wherein the conductive cloth comprises nylon and silver.

12. The method of claim 8, wherein the at least one inertial measurement unit comprises a 3-axis gyroscope, 3-axis accelerometer, and 3-axis magnetometer.

13. The method of claim 10, wherein the training and categorizing are based on machine learning algorithms.

* * * * *